US009427253B2

(12) United States Patent
Panian

(10) Patent No.: US 9,427,253 B2
(45) Date of Patent: Aug. 30, 2016

(54) DEVICE FOR APPLYING MEDICAL FLUID TO AN AREA AND FOR CUTTING WITHIN THE AREA

(75) Inventor: Tyler Devin Panian, Long Beach, CA (US)

(73) Assignee: CAREFUSION 303, INC., San Diego, CA (US)

( * ) Notice: Subject to any disclaimer, the term of this patent is extended or adjusted under 35 U.S.C. 154(b) by 378 days.

(21) Appl. No.: 13/274,980

(22) Filed: Oct. 17, 2011

(65) Prior Publication Data

US 2013/0096487 A1 Apr. 18, 2013

(51) Int. Cl.
| | |
|---|---|
| A61B 17/3209 | (2006.01) |
| A61B 17/3211 | (2006.01) |
| A61M 35/00 | (2006.01) |
| A61M 5/158 | (2006.01) |
| A61M 39/02 | (2006.01) |

(52) U.S. Cl.
CPC ....... *A61B 17/3209* (2013.01); *A61B 17/3211* (2013.01); *A61B 90/80* (2016.02); *A61B 2217/007* (2013.01); *A61M 35/003* (2013.01); *A61M 2005/1585* (2013.01); *A61M 2039/0232* (2013.01); *Y10T 29/49826* (2015.01)

(58) Field of Classification Search
CPC .......... A61B 17/3203; A61B 17/3209; A61B 17/32093; A61B 17/3211; A61B 2017/32032; A61B 2017/32035; A61B 2018/00571; A61B 2018/00601
USPC ............. 604/22, 46, 47, 506, 112, 264, 272; 606/45
See application file for complete search history.

(56) References Cited

U.S. PATENT DOCUMENTS

| | | | | |
|---|---|---|---|---|
| 878,524 | A * | 2/1908 | Gregory | 30/123.3 |
| 1,333,745 | A * | 3/1920 | Wescott | 452/69 |
| 1,484,618 | A * | 2/1924 | Blades | 452/131 |
| 3,786,814 | A * | 1/1974 | Armao | 606/23 |
| 4,297,765 | A * | 11/1981 | Altman | A22C 25/02 401/207 |
| 4,832,683 | A * | 5/1989 | Idemoto et al. | 604/22 |
| 4,858,324 | A * | 8/1989 | Wiech, Jr. | 30/357 |
| 5,288,274 | A * | 2/1994 | Bell | A63J 5/00 222/78 |
| 5,403,318 | A * | 4/1995 | Boehringer | A61B 17/14 606/178 |

(Continued)

FOREIGN PATENT DOCUMENTS

| | | |
|---|---|---|
| DE | 8421994 U1 | 11/1985 |
| DE | 4227369 C1 | 2/1994 |

(Continued)

OTHER PUBLICATIONS

Extended European Search Report for Application No. 12841119, dated May 28, 2015, 5 pages.

(Continued)

*Primary Examiner* — Andrew Gilbert
(74) *Attorney, Agent, or Firm* — McDermott Will & Emery LLP

(57) ABSTRACT

A device for applying medical fluid to an area and for cutting within the area is provided. The device includes an inlet port, a fluid flow channel, an outlet and a blade. The inlet port is configured for receiving the medical fluid into the device. The fluid flow channel is configured for the fluid to flow through the device. A first end of the fluid flow channel is connected to the inlet port. An outlet is configured for the fluid to come out of the device. The outlet is positioned at a second end of the fluid flow channel. The blade is configured for cutting within the area.

16 Claims, 8 Drawing Sheets

(56) References Cited

U.S. PATENT DOCUMENTS

| | | | |
|---|---|---|---|
| 5,460,182 A * | 10/1995 | Goodman et al. | 600/342 |
| 5,571,071 A * | 11/1996 | Shapiro | A61B 1/267 600/185 |
| 5,782,851 A * | 7/1998 | Rassman | 606/167 |
| 5,843,108 A * | 12/1998 | Samuels | 606/167 |
| 5,890,630 A * | 4/1999 | Lobdell | B65D 35/36 222/192 |
| 5,894,959 A * | 4/1999 | Sigurlidason | A47G 21/005 222/192 |
| 6,224,574 B1 * | 5/2001 | Al-Labban | A61M 5/178 604/187 |
| 6,352,465 B1 * | 3/2002 | Heymann | A63H 33/009 30/123.3 |
| 6,379,371 B1 * | 4/2002 | Novak et al. | 606/169 |
| 6,592,564 B2 * | 7/2003 | Finch et al. | 604/500 |
| 6,832,995 B1 * | 12/2004 | Towler | A61B 18/06 606/27 |
| 7,097,642 B1 * | 8/2006 | Sprague et al. | 606/27 |
| 7,293,989 B2 * | 11/2007 | Boiteux et al. | 433/82 |
| 7,625,268 B2 * | 12/2009 | Durjan | B26B 13/22 452/103 |
| 8,046,057 B2 * | 10/2011 | Clarke | 600/478 |
| 8,051,570 B1 * | 11/2011 | Brown | A47G 21/004 222/192 |
| 2001/0018594 A1 * | 8/2001 | Krag | 606/185 |
| 2002/0040231 A1 | 4/2002 | Wysoki | |
| 2002/0045907 A1 * | 4/2002 | Sherman et al. | 606/131 |
| 2002/0092521 A1 * | 7/2002 | Sullivan et al. | 128/200.24 |
| 2004/0087992 A1 * | 5/2004 | Gartstein et al. | 606/186 |
| 2005/0273097 A1 * | 12/2005 | Ryan | 606/45 |
| 2006/0206117 A1 * | 9/2006 | Harp | A61B 17/1624 606/85 |
| 2010/0274236 A1 * | 10/2010 | Krimsky | 606/21 |

FOREIGN PATENT DOCUMENTS

| | | |
|---|---|---|
| EP | 0456470 A1 | 11/1991 |
| WO | WO-2008/148139 A1 | 12/2008 |

OTHER PUBLICATIONS

International Search Report and Written Opinion for Application No. PCT/US2012/060308, dated Mar. 29, 2013, 9 pages.

* cited by examiner

DEVICE FOR APPLYING MEDICAL FLUID TO AN AREA AND FOR CUTTING WITHIN THE AREA

FIELD OF THE INVENTION

The present technology relates generally to medical devices for cutting a patient. More particularly, the present technology relates to applying medical fluid to an area and cutting within the area.

BACKGROUND

Various types of cutting devices have been used, for example, to make incisions in patients. Examples of cutting devices include, but are not limited to, razor blades and scalpels.

DRAWINGS

The drawings referred to in this description should not be understood as being drawn to scale unless specifically noted.

DESCRIPTION OF EMBODIMENTS

Before making an incision in an area of a patient, the area is sterilized with disinfectant fluid. The doctor takes a reservoir of medical fluid, such as a syringe with disinfectant in it, and applies the fluid to the patient. The doctor then has to remove the reservoir from their hand in order to grasp a cutting device with a blade. The operation of picking up the reservoir, putting the reservoir down, then picking up the cutting device is awkward and can lead to errors. Therefore, according to one embodiment, a device is provided that can be used for both applying the fluid and cutting, as will become more evident. According to one embodiment, a device is provided that can be used to improve the health of the patient.

Although various embodiments are described in the context of the fluid being a disinfectant, embodiments are well suited to other types of fluid, such as lubricant or solvent. According to one embodiment, the fluid is intended for medical use. According to one embodiment, the fluid is sterile.

Figure 1A:
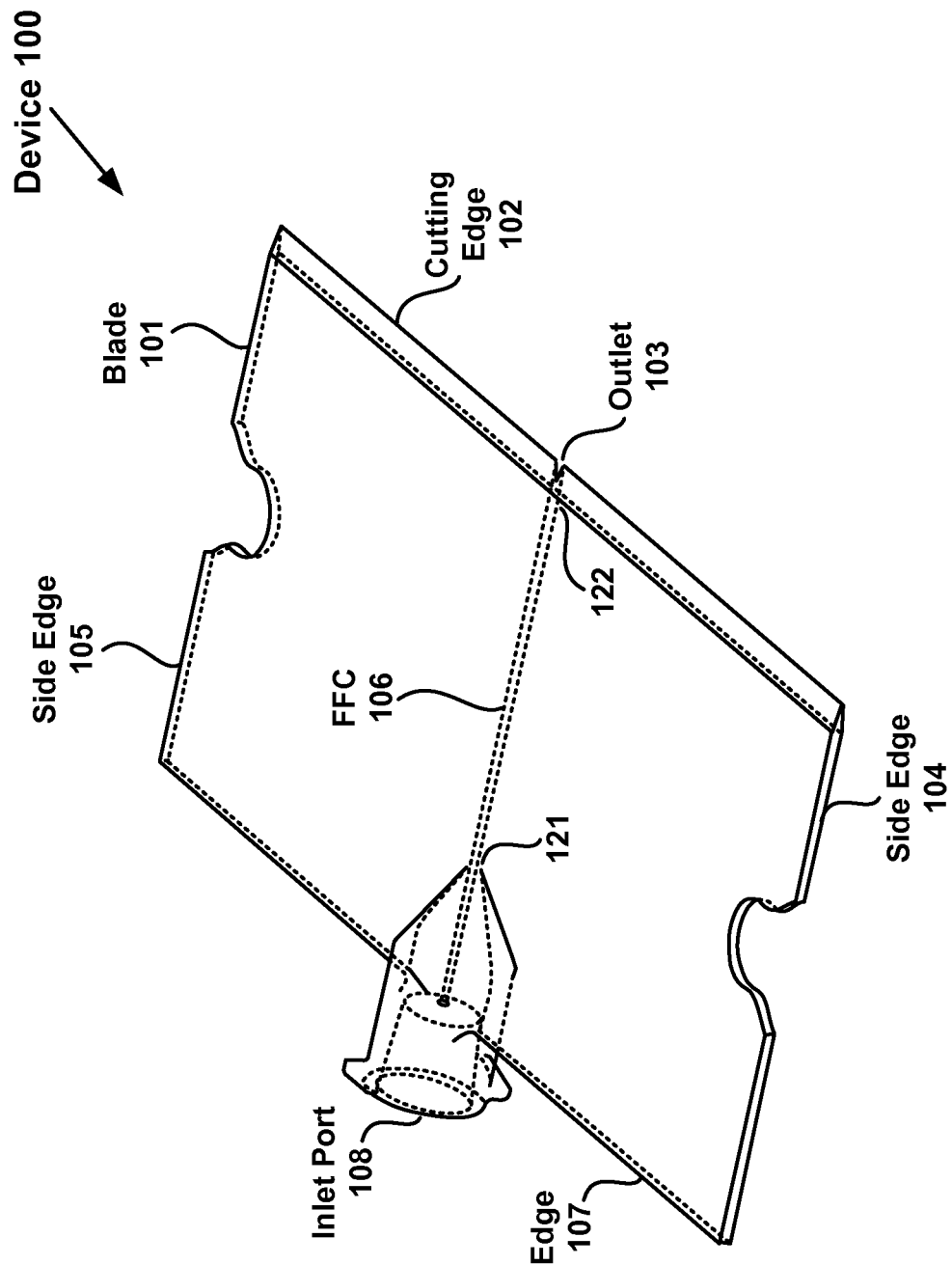
FIG. 1A depicts a device for applying fluid and cutting a patient from an angled view, according to one embodiment.
Figure 1B:
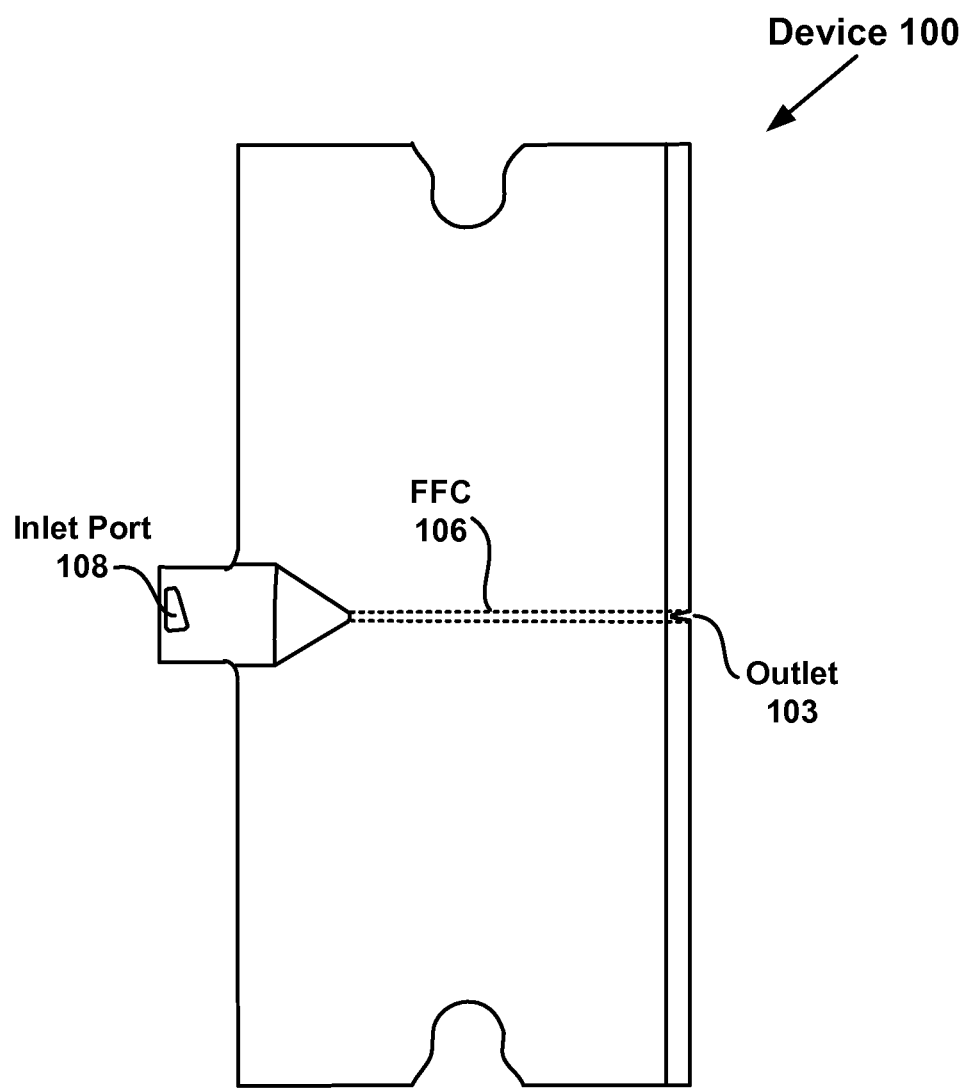
FIG. 1B depicts a top down view of the device, according to one embodiment.

FIG. 1A depicts a device 100 for applying fluid and cutting a patient from an angled view, according to one embodiment. FIG. 1B depicts a top down view of the device 100, according to one embodiment. The device 100 includes an inlet port 108, a fluid flow channel (FFC) 106, an outlet 103, and a blade 101.

The device 100 includes a blade 101 for cutting the patient. FIGS. 1A, 1B depict a blade 101 with a straight cutting edge. However, embodiments are well suited for other blade configurations. For example, the blade 101 may be curved. The blade 101 may be made out of various types of materials, such as different types of metal.

As depicted in FIGS. 1A, 1B, the blade 101 is similar to a razor blade. However, embodiments are well suited for blade configurations that are similar to other types of cutting devices, such as a scalpel or an exacto knife, among other things.

As depicted in FIGS. 1A, 1B, the device 100 does not include a separate handle. However, embodiments are well suited to a device 100 that includes a handle.

The inlet port 108 is configured for receiving the fluid into the device 100. For example, the inlet port 108 can be configured to receive fluid from a reservoir of fluid. Examples of reservoirs include, but are not limited to, a syringe or a bottle. An outlet port of the reservoir may be inserted into the device 100's inlet port 108. The inlet port 108 may be designed to function with a particular type of reservoir. For example, the size and shape of the inlet port may be compatible with a reservoir's outlet port. In another example, the inlet port 108 may have threads that, that for example, mate with threads associated with the reservoir's outlet. However, the inlet port 108 may not have threads.

In another embodiment, the inlet port 108 may be a universal port that is designed to function with a wide variety of reservoirs. The size and shape of the inlet port 108 may be designed to be large enough to accommodate a wide variety of reservoirs. The device 100's inlet port 108 may have material that expands when a reservoir's outlet port is inserted into the device 100's inlet port 108 and contracts, for example, when the reservoir's outlet port is extracted from the device 100's inlet port 108.

As depicted in FIGS. 1A and 1B, the inlet port 108 is oriented in the center of the non-cutting edge 107 that is opposite the cutting edge 102. However, embodiments are well suited for other orientations of the inlet port 108. For example, the inlet port 108 may be positioned on any non-cutting edge 107, 104, 105 of the device 100. More specifically, the inlet port 108 may be positioned on a side 104, 105 of the device 100, a side 104, 105 of a blade 101, on a handle of the device, on a spine of the device, among other things. Further, the inlet port 108 may be oriented at any position along an edge 104, 105, 107, a handle or a spine. For example, the inlet port 108 may be located in the center of an edge 104, 105, 107, off of the center of the edge 104, 105, 107, on a tip of a device, or a handle, among other things.

The fluid flow channel 106 includes a first end 121 that is connected to the inlet port 108. The device 100 also includes a fluid flow channel 106 configured for the fluid to flow through the device 100. According to one embodiment, the fluid flow channel 106 is a narrow channel. As depicted in FIGS. 1A and 1B, the device 100 includes a single FFC 106. However, embodiments are well suited for a plurality of FFCs, for example, to more evenly distribute the fluid, as will become more evident.

As depicted in FIG. 1A, the FFC 106 is straight and is located down the center of the blade 101. However, embodiments are well suited for other orientations and configurations of the FFC 106. For example, the FFC 106 may be non-straight, the FFC 106 may be bent, the FFC 106 may be located off of the center of the device 100 or the blade 101, the FFC 106 may be located on the blade 101 or off of the blade 101, the FFC 106 may be located in a handle or a spine of a device.

An outlet 103 is at the other end 122 of the FFC 106 where the fluid exits the FFC 106. As depicted in FIGS. 1A, 1B the outlet 103 is located in the center of the cutting edge 102.

Embodiments are well suited to other orientations for the outlet 103. For example, the outlet 103 may be located on a cutting edge 102 or a non-cutting edge 104, 105, 107. Non-cutting edges can include edges along a handle, a spine, or the non-cutting side of a blade, among others. Further, the outlet 103 may be oriented at any position along a cutting edge 102 or non-cutting edge 104, 105, 107, handle or spine. For example, the outlet 103 may be located in the center of an edge, off of the center of the edge, on a tip of the device, the blade, or spine, at any position along a handle, blade or a spine, among other things.

An outlet 103 may be the same width as the FFC 106, wider than the FFC 106, or narrower than the FFC 106.

Figure 2:
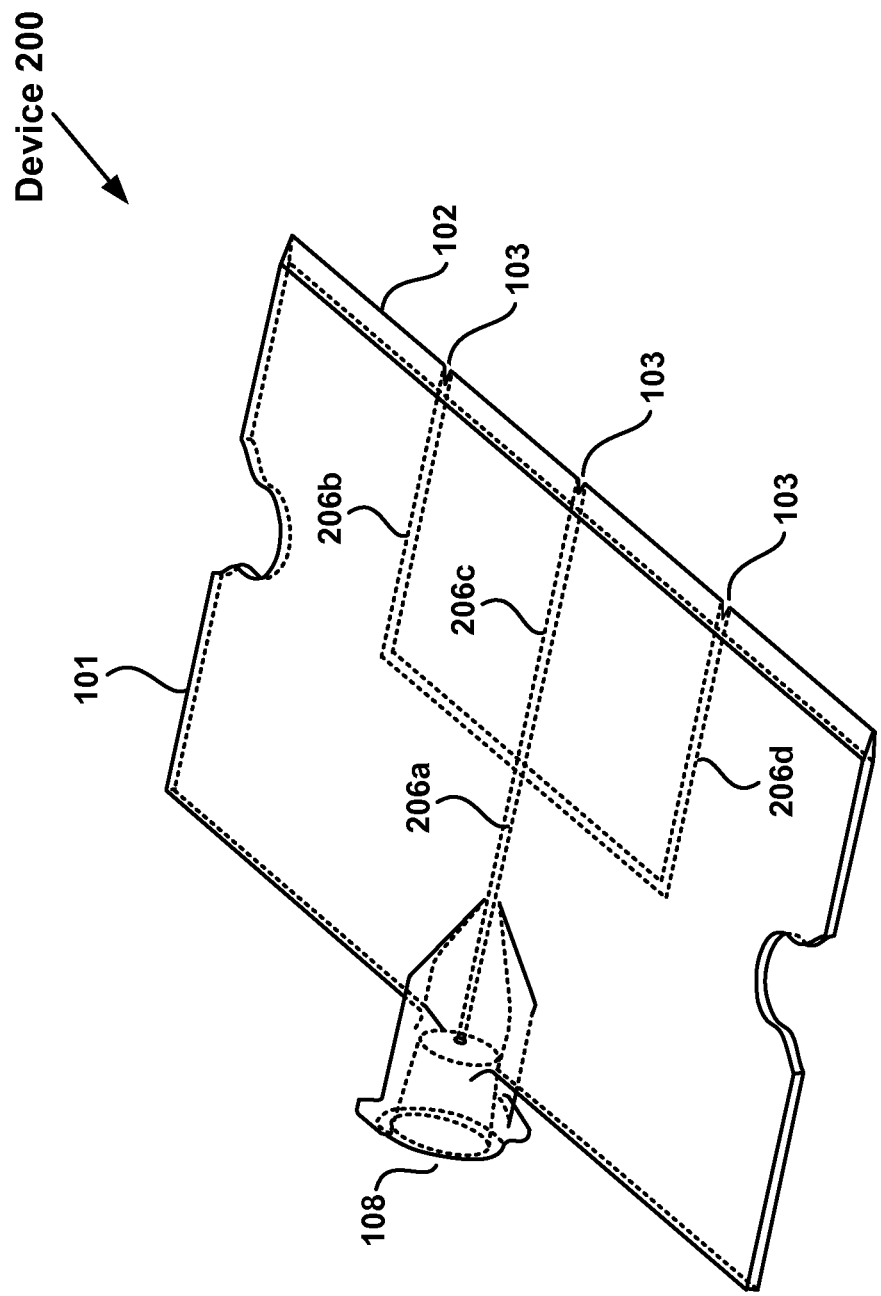
FIG. 2 depicts a device with a multiple channel fluid flow channel, according to one embodiment.

FIG. 2 depicts a device 200 with a multiple channel fluid flow channel, according to one embodiment. As depicted in FIG. 2, the device includes a FFC 206 with multiple channels 206a-206d. The FFC 206 initially includes a single channel 206a, which is connected to the inlet port 108, and the single channel 206a then branches into multiple channels 206b-206d. Multiple outlets 103 can oriented evenly or unevenly along an edge 102.

According to other embodiments, the FFC may include several channels that connect with the inlet port 108. Embodiments are well suited for other orientations and locations of a multiple channel FFC.

Figure 3:
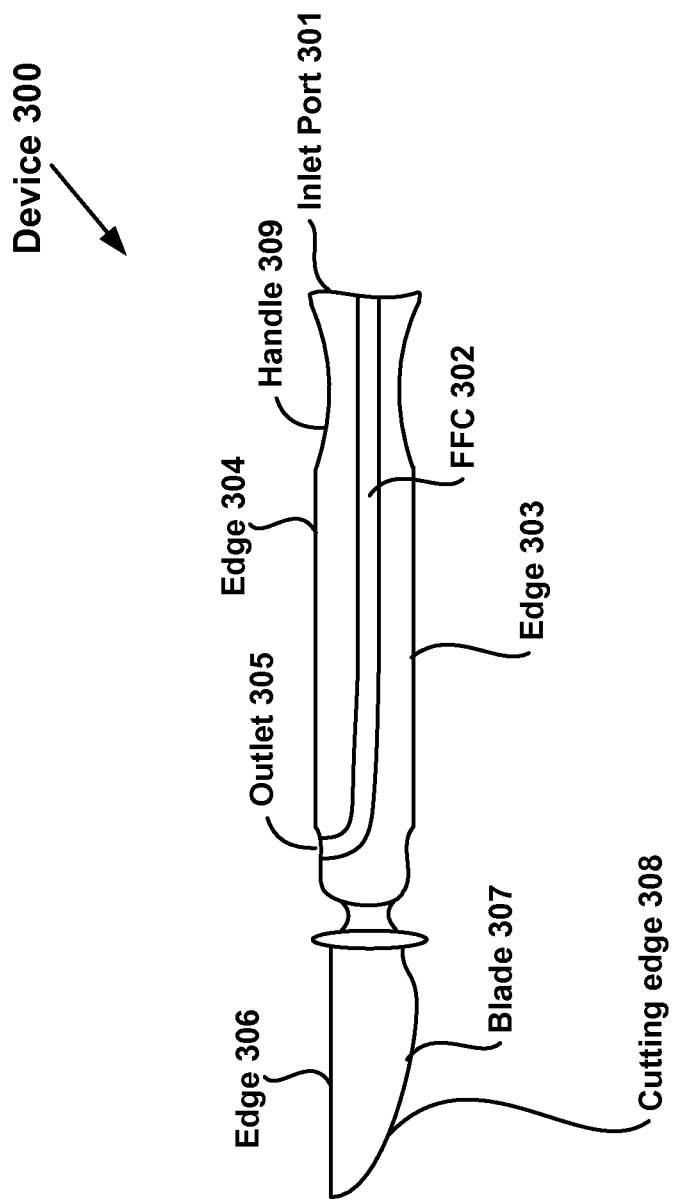
FIG. 3 depicts a device with a handle, according to one embodiment.

FIG. 3 depicts a device 300 with a handle 309, according to one embodiment. For example, the device 300 includes a handle 309, a FFC 302, an inlet port 301, an outlet 305 and a blade 307. The blade 307 is attached to one end of the handle 309. The inlet port 301 is connected to the other end of the handle 309. The outlet 305 is oriented on the side of the device 300 and at one end of the handle 309. The fluid flow channel 302 runs through the handle 309 and is bent. One edge 308 of the blade 307 is curved.

As depicted in FIG. 3, the inlet port 301 is oriented approximately toward the center of one end of the handle 309. Similarly, the FFC 302 is oriented approximately in the center of the handle 309. However, embodiments are well suited to other orientations of the inlet port 301 and the FFC 302.

Although FIG. 3 depicts the handle 309 attached to one end of the blade 307, embodiments are well suited for the handle 309 to be located at other locations and in other orientations. For example, a handle could be oriented along a non-cutting edge such as the non-cutting edges 104, 105, 107 of device 100 depicted in FIGS. 1A, 1B.

Figure 4:
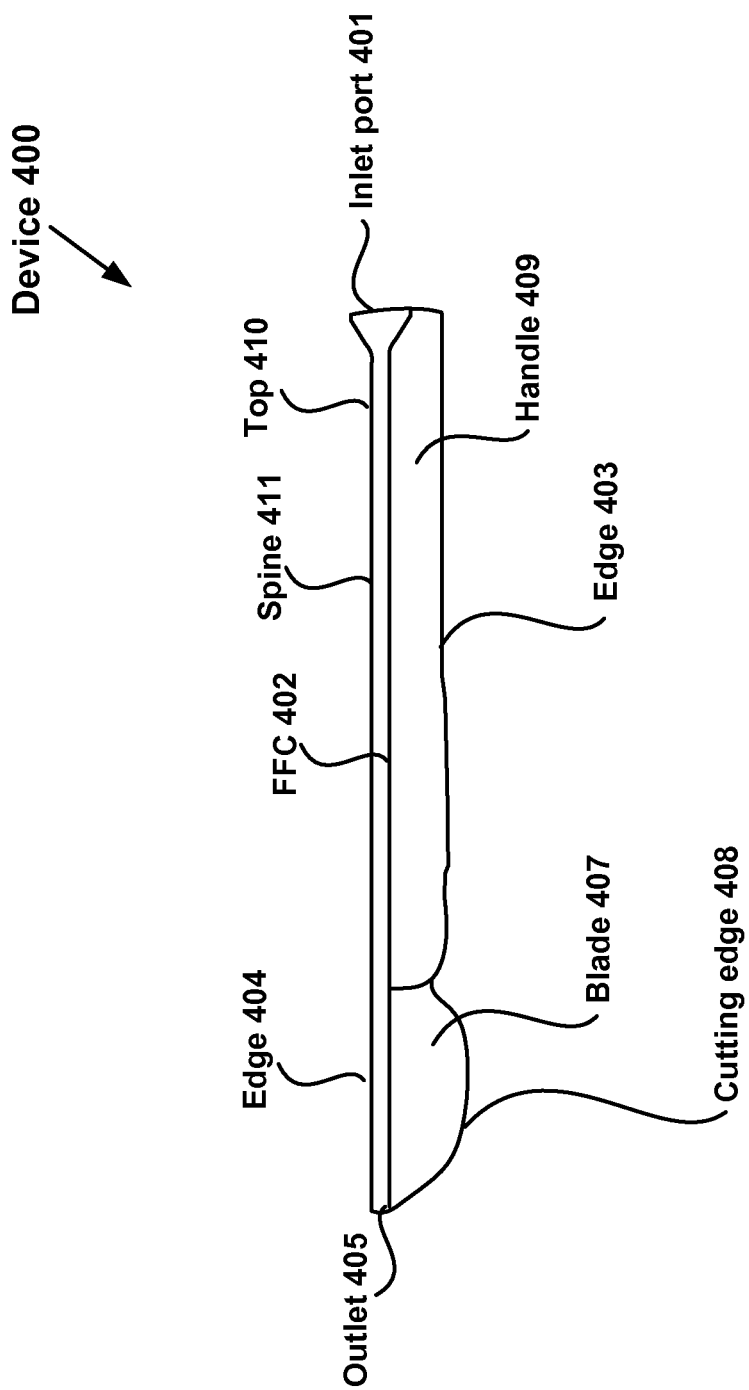
FIG. 4 depicts a device with a spine, according to one embodiment.

FIG. 4 depicts a device 400 with a spine 411, according to one embodiment. For example, the device 400 includes a handle 409, a spine 411, a FFC 402, an inlet port 401, an outlet 405 and a blade 407. The blade 407 is oriented toward one end of the handle 409, according to one embodiment. The inlet port 401 is oriented toward the other end of the handle 409. The device 400 includes a spine 411 that runs along the top 410 of the handle 409 and the non-cutting edge 404 of the blade 407. The FFC 402 runs through the spine 411, according to one embodiment. The spine 411 may be part of the handle 409 or may be separate from the handle 409. The inlet port 401, according to one embodiment, is aligned with the FFC 402 that runs through the spine 411.

As depicted in FIGS. 1A, 2, 3, and 4 examples of cutting edges include cutting edges 102, 308, 408, among other things, and examples of non-cutting edges include edges 104, 105, 107, 303, 304, 306, 403, 404, among other things.

Figure 5:
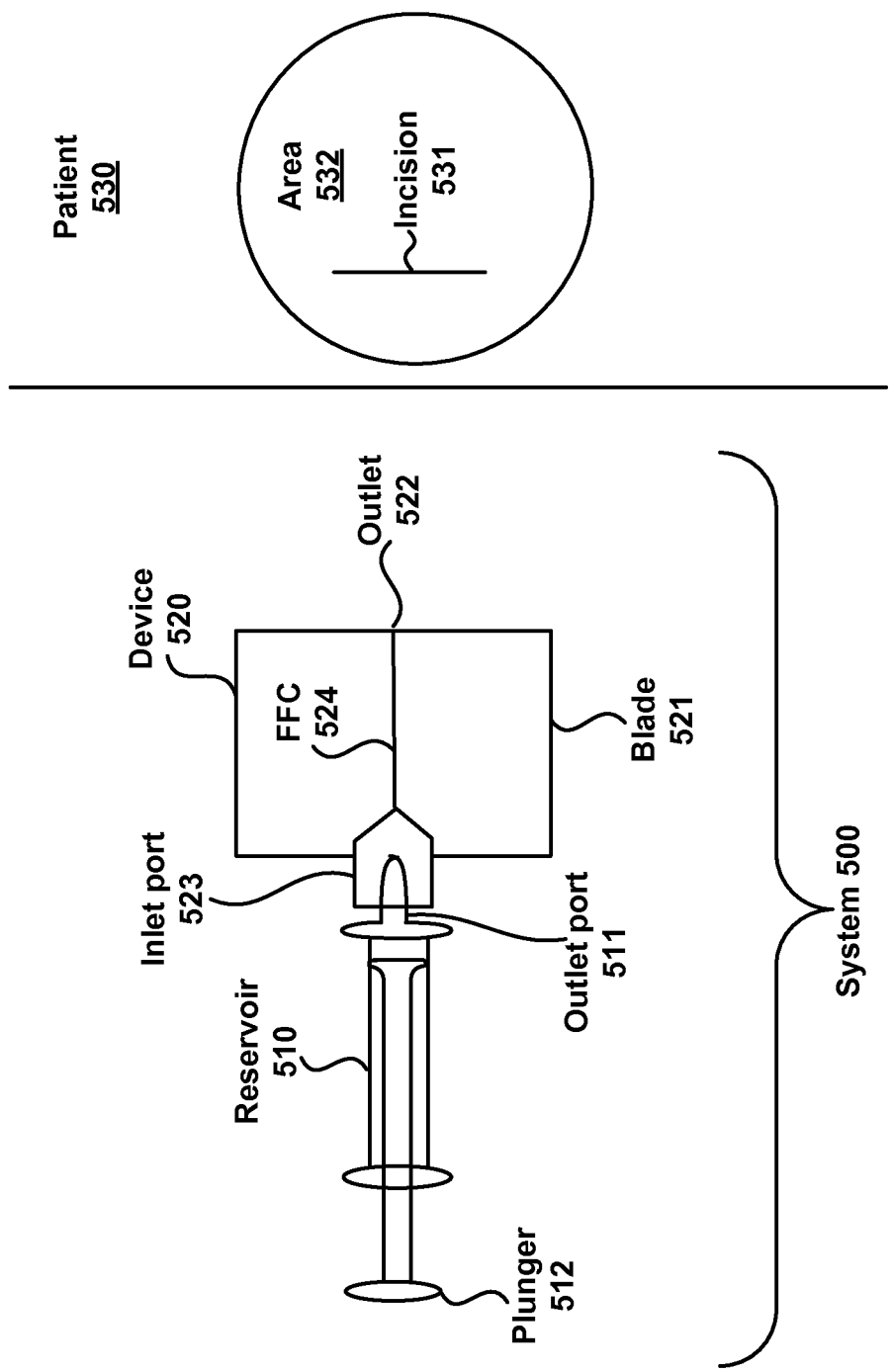
FIG. 5 depicts a system for applying fluid and cutting a patient, according to one embodiment.

FIG. 5 depicts a system 500 for applying fluid to an area 532 and for cutting within the area 532, according to one embodiment. System 500 depicts a reservoir 510, such as a syringe and a device 520. The reservoir 510 is connected with the device 520. For example, an outlet port 511 associated with the reservoir 510 is inserted into the device 520's inlet port 523. Fluid can be delivered from the reservoir 510, through the device 520, out the device's outlet 522 and to an area 532 of the patient 530. An incision 531 is depicted within the area 532 of the patient 530 using the device 520's blade 521. The incision 531 in the patient 530 may be any depth or length depending on the type of procedure being performed on the patient 530.

Figure 6:
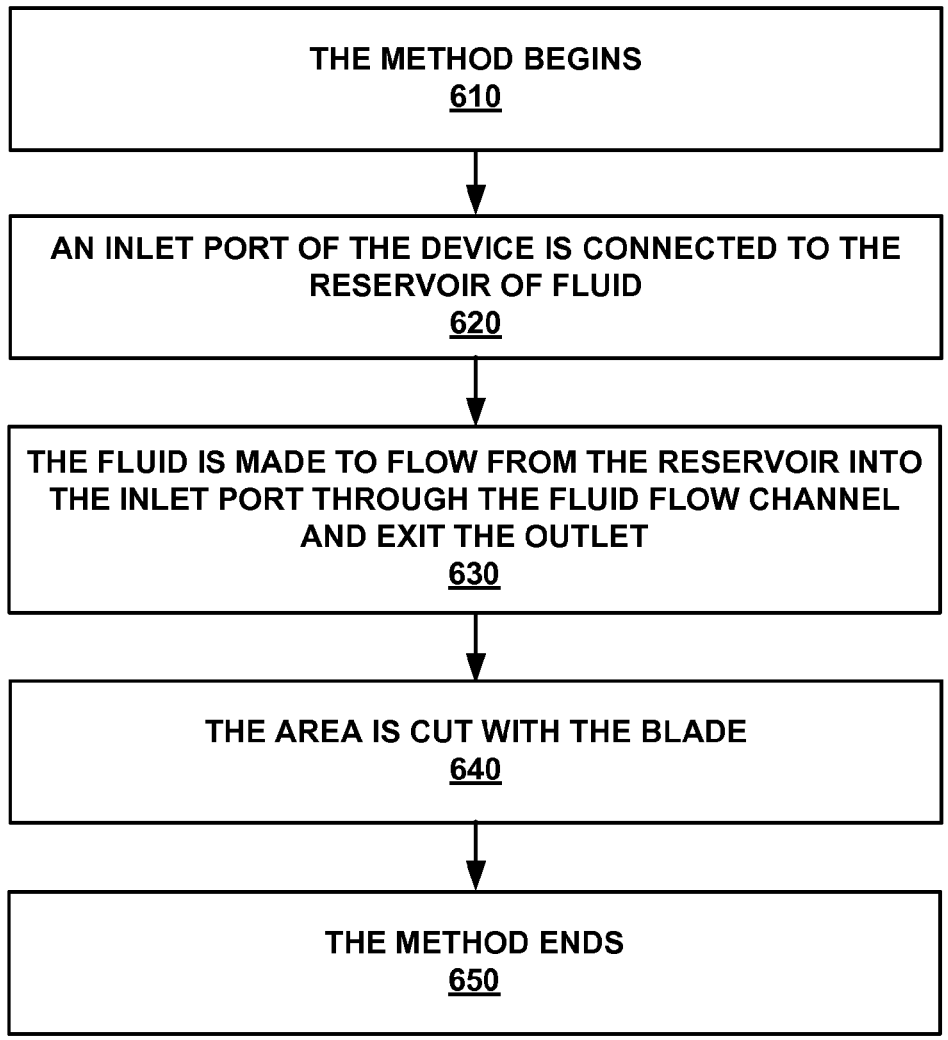
FIG. 6 depicts a flow chart for a method of using a device, according to one embodiment.

FIG. 6 depicts a flow chart 600 of a method for using a device, according to one embodiment. FIG. 6 is described in the context of FIG. 5.

At 610, the method begins.

At 620, an inlet port 523 of the device 520 is connected to a reservoir 510 of fluid. As depicted in FIG. 5, the outlet port 511 of a reservoir 510, such as a syringe, is inserted into the device 520's inlet port 523.

The device 520 has a fluid flow channel 524 for the fluid to flow through the device 520, an outlet 522 for the fluid to exit the device 520 for application to an area 532, for example, of a patient 530, and a blade 521 for cutting within the area 532.

At 630, the fluid is made to flow from the reservoir 510 into the inlet port 523 through the fluid flow channel 524 and exit the outlet 522. The device 520's inlet port 523 receives the fluid from the reservoir 510. For example, a doctor or clinician pushes the syringe's plunger 512 causing the fluid to flow out of the syringe 510's outlet port 511 and into the device 520's inlet port 523. The fluid proceeds to flow through the device 520's FFC 524 and out the device 520's outlet 522 onto the area 532 of the patient 530. Although embodiments have been described in the context of a person pushing a plunger 512 to deliver medical fluid, embodiments are well suited to other actions for causing the fluid to be delivered. For example, a bottle containing medical fluid could be squeezed.

At 640, the area 532 is cut with the blade 521. For example, the blade 521 is used to make the incision 531 within the area 532 of the patient 530.

At 650, the method ends.

The doctor or clinician can use an edge of the device 520 to distribute the fluid evenly in an area 532 on the patient, for example, before the blade 521 is used to make the incision 531 in that area 532.

Figure 7:
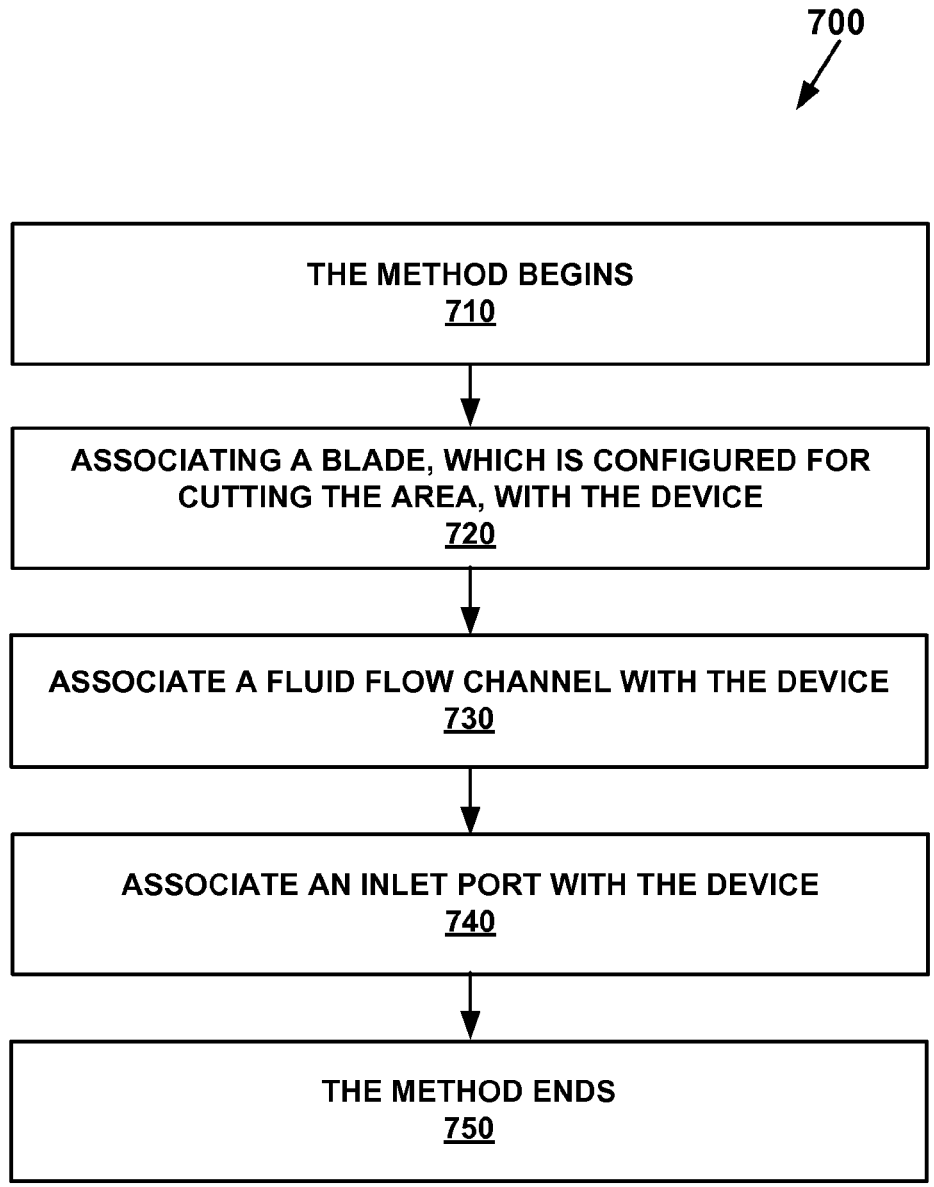
FIG. 7 depicts a flow chart for method of making a device, according to one embodiment.

FIG. 7 depicts a flowchart 700 of a method for making a device, according to one embodiment. FIG. 7 is described in the context of FIGS. 1-4.

At 710, the method begins.

At 720, a blade 101, 307, 407, which is configured for cutting the patient, is associated with the device 100, 200, 300, 400. According to one embodiment, the blade 101, 307, 407 can be made of various types of materials, such as various types of steel. The blade 101, 307, 407 may be straight, such as a razor blade, curved like a scalpel, or angled like an exacto knife. The blade 101, 307, 407 may be made of a single piece or multiple pieces of material. For example, the blades 307, 407 depicted in FIGS. 3 and 4 are made of a single piece of material. The blades 101 depicted in FIGS. 1A, 1B, 2 may be made of a single piece of material where the single piece of material is configured with the FFC running through the single piece of material or may be made, for example, of two pieces that are attached to the FFC.

At 730, a fluid flow channel 106, 206, 302, 402 is associated with the device 100, 200, 300, 400. The fluid flow channel 106, 206, 302, 402 is configured for the fluid to flow through the device 100, 200, 300, 400. Referring to FIGS. 1A, 1B, 2 the blade 101 may be configured to include the FFC 106, 206 or the blade 101 may be attached to another piece that includes the FFC 106, 206. Referring to FIGS. 3 and 4, a handle 309, 409 or a spine 411 may include the FFC 302, 402. The blade 307, 407 can then be attached to the handle 309, 409. In another embodiment, any two or more of the blade, handle, spine and FFC may be made out of a single piece of material instead of attaching the various pieces, such as the blade and the handle, to each other.

At 740, an inlet port 108, 301, 401 is associated with the device 100, 200, 300, 400. The inlet port 108, 301, 401 may be made out of separate piece of material that is attached to the device 100, 200, 300, 400. According to another embodiment, the inlet port 108, 301, 401 may be made out of the same piece of material as the rest of the device or may be made out of a separate piece of material as the rest of the device. In another example, the inlet port 301, 401 may be made out of the same piece of material as the handle 309, 409. The handle 309, 409 may or may not be made out of the same piece of material as the rest of the device. If the handle 309, 409 and the rest of the device are separate pieces of material, then they can be attached.

The inlet port 108, 301, 401 and the fluid flow channel 106, 206 may be made out of the same piece of material as the blade 101. The inlet port 108, 301, 401 and the fluid flow channel 106, 206, 302, 402 can be made out of a different piece of material than the blade 101, 307, 407 where the blade 101, 307, 407 is then attached directly or indirectly to the inlet port fluid flow channel combination.

The device 100, 200, 300, 400 is configured for fluid to flow from the inlet port 108, 301, 401 through the fluid flow channel 106, 206, 302, 402 and to exit an outlet 103, 305, 405 of the device 100, 200, 300, 400 for application to an area 532, for example, of a patient or an item.

At 750, the method ends.

Although various embodiments have been described in the context of making an incision in a patient, various embodiments can be used for cutting something other than a patient. For example, a device could be used to lubricate an area of an item, such as a piece of tubing, another medical device, among other things, and then cut inside of the area. In this case, a portion of the item would be an example of an area that fluid is applied to and that the blade is used to cut within.

Various embodiments have been described in various combinations and illustrations. However, any two or more embodiments or features may be combined. Further, any embodiment or feature may be used separately from any other embodiment or feature. Phrases, such as "an embodiment," "one embodiment," among others, used herein, are not necessarily referring to the same embodiment. Features, structures, or characteristics of any embodiment may be combined in any suitable manner with one or more other features, structures, or characteristics.

What is claimed is:

1. A device for applying medical fluid to an area and for cutting within the area, the device comprising:
   a blade made of a single piece of material and comprising:
      an inlet port positioned on a non-cutting edge of the blade and sized and shaped for coupling via insertion to an outlet port of a fluid reservoir in order to receive the medical fluid from the outlet port into the device;
      a fluid flow channel configured for the medical fluid to flow through the device, a first end of the fluid flow channel connected to the inlet port, wherein the fluid flow channel branches into a plurality of channels having respective outlets, the outlets configured for the medical fluid to come out of the device to sterilize the area; and
      a straight cutting edge provided parallel to the non-cutting edge, on which the inlet port is positioned, and configured for cutting in the area that the medical fluid has been applied to,
      wherein each of the outlets forms a gap along the straight cutting edge of the blade.

2. The device of claim 1, wherein the inlet port mates with the outlet port of the fluid reservoir via the coupling.

3. The device of claim 2, wherein the inlet port has threads that mate with threads of the outlet port of the fluid reservoir.

4. The device of claim 1, wherein the inlet port is a universal inlet port that is compatible with various types of fluid reservoir outlet ports.

5. The device of claim 1, wherein the inlet port is located at any position on the non-cutting edge of the blade.

6. The device of claim 1, wherein the device includes a handle.

7. The device of claim 6, wherein the fluid flow channel is located, at least in part, in the handle.

8. The device of claim 1, wherein each of the outlets is located at any position along the straight cutting edge of the blade.

9. The device of claim 1, wherein the medical fluid comprises a liquid.

10. A method of using a device for applying medical fluid to an area and for cutting within the area, the method comprising:
    connecting an inlet port positioned on a non-cutting edge of a blade of the device to a reservoir of medical fluid via insertion of an outlet port of the reservoir of the medical fluid into the inlet port, the inlet port sized and shaped for coupling to the outlet port of the reservoir, wherein the blade further comprises a straight cutting edge provided parallel to the non-cutting edge, on which the inlet port is positioned, for cutting in the area, the blade comprising a single piece of material, a fluid flow channel for the medical fluid to flow through the device, and outlets each forming a gap along the straight cutting edge of the blade;
    causing the medical fluid to flow from the reservoir into the inlet port positioned on the non-cutting edge of the blade through the fluid flow channel, wherein the fluid flow channel branches into a plurality of channels corresponding to the outlets, wherein the medical fluid exits via the outlets to sterilize the area; and
    cutting with the straight cutting edge of the blade in the area.

11. The method as recited by claim 10, wherein the method further comprises:
    using an edge of the device to distribute the medical fluid in the area.

12. The method as recited by claim 11, wherein using an edge of the device to distribute the medical fluid in the area comprises using at least a portion of the straight cutting edge of the blade.

13. The method as recited by claim 10, wherein connecting an inlet port of the device to a reservoir of medical fluid comprises inserting a syringe to the inlet port of the device.

14. The method as recited by claim 13, wherein causing the medical fluid to flow from the reservoir into the inlet port comprises pushing a plunger in the syringe.

15. The method as recited by claim 10, wherein the device for applying medical fluid comprises a bottle containing the medical fluid, and causing the medical fluid to flow from the reservoir into the inlet port comprises squeezing the bottle.

16. The method as recited by claim 10, wherein causing the medical fluid to flow from the reservoir into the inlet port comprises causing one of a lubricant fluid and a solvent fluid to flow through the fluid flow channel into the area.

* * * * *